Figure 1:
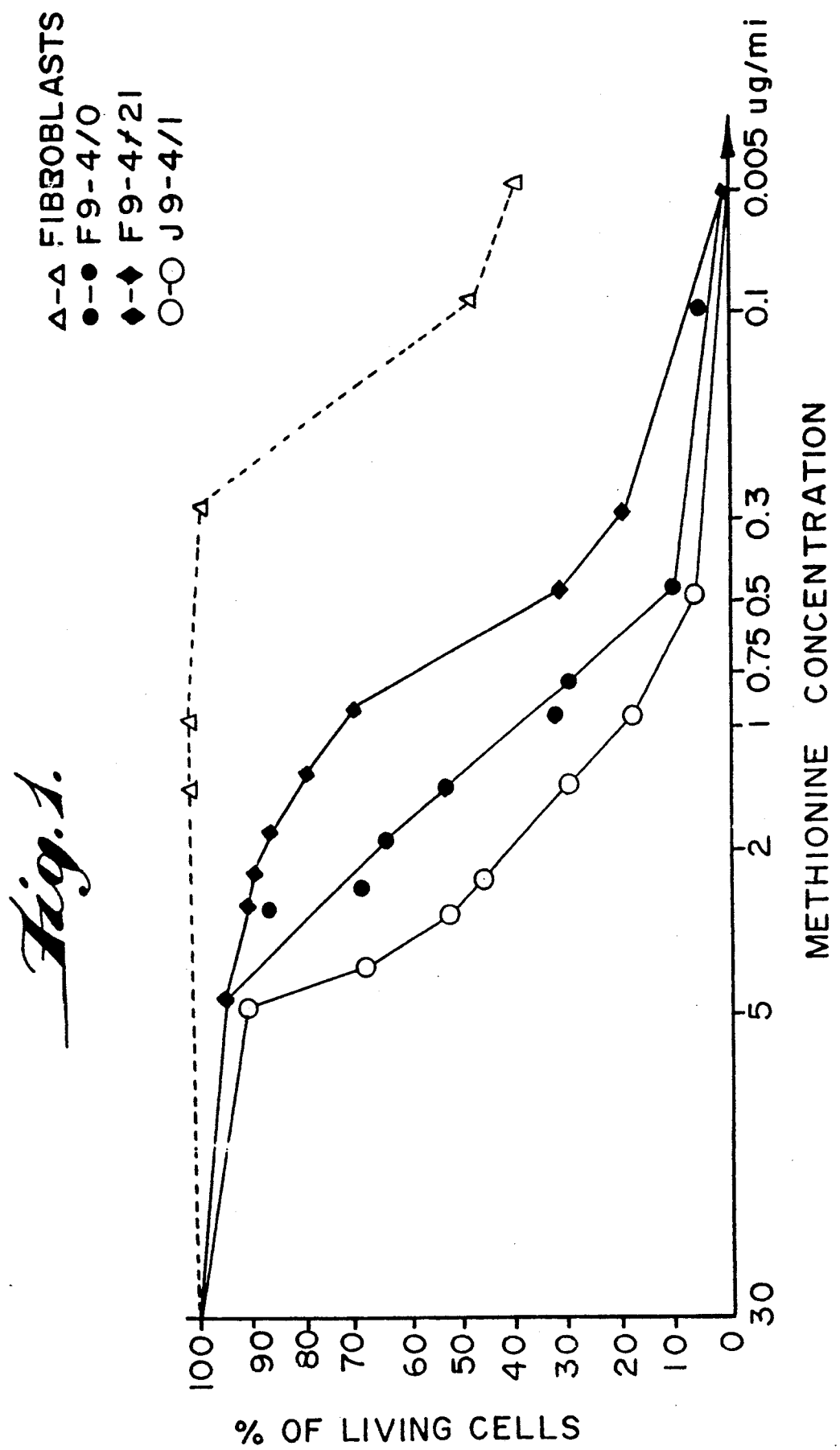

United States Patent [19]

Poupon et al.

[11] Patent Number: 5,208,039
[45] Date of Patent: May 4, 1993

[54] NUTRIENT COMPOSITIONS DEPRIVED OF METHIONINE AND SUPPLEMENTED WITH HOMOCYSTEINE

[75] Inventors: Marie-France Poupon, Fresnes; Paule Echinard-Garin, Sceaux; Fabienne R. Breillout, Paris, all of France

[73] Assignee: Centre National de la Recherche Scientifique (CNRS), Paris, France

[21] Appl. No.: 457,194

[22] Filed: Dec. 26, 1989

Related U.S. Application Data

[63] Continuation of Ser. No. 98,026, Oct. 6, 1987, abandoned.

[51] Int. Cl.$^5$ ............................................... A61K 9/16
[52] U.S. Cl. ................................... 424/490; 424/439; 424/440; 424/441
[58] Field of Search ................ 424/439, 440, 441, 490

[56] References Cited

U.S. PATENT DOCUMENTS 3,626,003 12/1971 Kominato et al. .................. 548/112
3,819,480 6/1974 Hochschild ...................... 514/562 X
4,363,815 12/1982 Yu et al. ......................... 514/564 X
4,438,270 3/1984 Bey et al. ......................... 514/277 X
4,499,064 2/1985 Shive .............................. 435/240.31
4,657,866 4/1987 Kumar ............................ 435/240.31
4,902,718 2/1990 Bayless et al. ................... 514/877 X

OTHER PUBLICATIONS

Recommended Daily Allowances 10th ed. National Academy Press 1989.

Primary Examiner—Thurman K. Page
Assistant Examiner—D. Gabrielle Phelan
Attorney, Agent, or Firm—Cushman, Darby & Cushman

[57] ABSTRACT

Synthetic or semisynthetic nutrient composition intended to inhibit the development and the dissemination of malignant tumors in mammals, which composition is characterized in that it is deprived of methionine and supplemented with homocysteine; and utilization, in the preparation of such nutrient compositions, of a source of amino acids deprived of methionine.

28 Claims, 3 Drawing Sheets

NUTRIENT COMPOSITIONS DEPRIVED OF METHIONINE AND SUPPLEMENTED WITH HOMOCYSTEINE

This is a continuation of Application Ser. No. 07/098,026, filed Oct. 6, 1987, now abandoned.

The object of the present invention is nutritional compositions intended to inhibit the development and dissemination of malignant tumors, and in particular metastases in mammals.

It is known that the metastatic dissemination of malignant tumors represents, in the development of cancers, a phase whose prevention and treatment are very difficult. Present therapy uses radiotherapy and chemotherapy, as well as surgery, when the metastases are few and accessible. However, the results remain inadequate in numerous cases and it therefore appears necessary to seek new therapies.

It is also known that the metabolism of tumoral cells is different from that of normal cells and that in particular the in vitro proliferation of tumoral cells is dependent on the supply of exogenous methionine; see, for example, R. M. Hoffman, Biochem. Biophys, Acta 738, 49-87 (1984).

Although methionine is conventionally considered as an essential amino acid, the normal cell, even in the proliferation phase, has low sensitivity or is insensitive to the absence of methionine when such is replaced, particularly with homocysteine in the presence of choline and vitamin B12. In effect, under such conditions, the normal cells can carry out their own synthesis of methionine which they then use in their metabolism. The tumoral cells are incapable of this.

It has now been discovered that a food lacking in methionine and supplemented with homocysteine particularly inhibits insignificant proportions the installation and the development of metastases in mammals.

The object of the present invention is a synthetic or semisynthetic nutritional composition intended to inhibit the development and the dissemination of malignant tumors in mammals, characterized by the fact that it is lacking in methionine and supplemented with homocysteine.

Among the compositions of the invention, those which correspond to a methionine deficiency of at least 50% will particularly be cited.

A composition lacking in methionine cannot be defined in the absolute since the needs of methionine vary in accordance with the species. For a given species, a composition lacking in methionine can be defined in the following manner. It is a balanced nutritional composition for a given animal species, containing y% by weight of methionine. It is considered that a composition is deficient by x% in methionine when said composition, which is identical to the balanced composition in all the other components contains only $$\frac{y(100-x)}{100} \%$$

by weight of methionine.

The invention relates in particular to a composition which contains, as the source of amino acids, a mixture of essential amino acids in appropriate proportions for the mammal in question, but with a reduced methionine content, and whose other ingredients are free of proteins or do not provide more than 1% in relation to the total dry weight of the components; among these compositions, those whose methionine content in the mixture of amino acids used is nil can particularly be cited.

In the composition of the invention, the homocysteine is added as a replacement for the methionine, that is that the homocysteine content corresponds, in molar equivalents, to the lack of methionine.

When the composition of the invention is intended to be administered enternally, it further contains sources of glucides and lipides, mineral salts, vitamins and possibly bulk ailments such as vegetable fibers. The source of amino acids other than the homocysteine can, in such case, be composed partially or solely of proteins which are low in methionine, for example, soya proteins or soya protein hydrolyzates.

Such a composition can, for example, be in the form of powder, aqueous suspension or emulsion, etc.

In order to improve the organoleptic properties of compositions intended for enteral administration, it is desirable for the homocysteine to be present in such compositions (or indeed as a separate composition to be added at the time of use) in a form coated by microcapsules with walls which are soluble in the digestive tracts, for example under the action of digestive enzymes. The materials constituting such microcapsules, as well as the methods for preparing such microcapsules, are known per se. In this regard, French Patent 2,527,438 can be cited which describes a method for encapsulation using microcapsules with walls composed of cross-linked polyholosides.

When the composition of the invention is intended to be administered parenterally, it is presented in the form of a homogenous fluid composition containing, in an aqueous isotonic vehicle, said amino acids and possibly glucides and mineral salts. Such compositions can be administered intravenously in man, for example. The mineral salts and the lipids can be administered intravenously, either separately or at the same time as the amino acids. The vitamins can be administered intramuscularly, for example.

In diets using the compositions of the invention, and in particular where the amino acid sources are synthetic amino acids, it is necessary to introduce choline. The choline can be administered separately, for example with the vitamins.

Of course, the compositions of the invention contain the nutritive substances and the vehicles or adjuvants in relative quantities and proportions such that the daily needs of the treated mammal are ensured by administration of an acceptable volume of composition for the mammal under consideration. The molar proportion of homocysteine corresponds to that of the missing methionine in relation to a balanced composition for the species under consideration.

The needs in glucides, lipides, amino acids, mineral salts and vitamins vary for each species and are either known or able to be determined in accordance with known methods.

The compositions of the invention can be administered upon discovery of a tumor, and in particular before or immediately after a surgical intervention. Of course, the treatment with the nutritional compositions lacking in methionine will generally be an additional treatment associated with other methods of therapy such as chemotherapy or radiotherapy.

The treatment can be continued, for example, for 1 to 4 months. The treatment can then be continued using a mixed diet of the vegetarian type.

The object of the invention is also a method for preparation of the compositions as defined above, by mixing the ingredients in suitable proportions and possibly with a suitable vehicle (water or physiological serum).

A further object of the invention is the use, in the preparation of nutritional compositions intended to inhibit the development and the dissemination of malignant tumors in mammals, of a source of amino acids lacking in methionine, with the missing methionine being replaced with homocysteine, as indicated above.

The invention also relates to a method for therapeutic treatment, intended to inhibit the development and the dissemination of malignant tumors in mammals, which method consists of feeding the patient, enterally or parenterally, with a composition lacking in methionine and supplemented in homocysteine, such as defined above, administered in sufficient quantity to satisfy nutritional needs.

One of the advantages of this treatment is particularly that it prevents the implantation and/or treats the micrometastases which are known to have low sensitivity to chemotherapy.

The following examples illustrate the invention without, however, limiting it.

EXAMPLES 1 TO 5

Semi-synthetic Compositions

A composition was prepared containing the following ingredients (Table 1):

TABLE 1

| Nutritional Ingredients | Example 1 - Composition for Mouse or Rat (g/kg of composition) |
| --- | --- |
| GLUCIDES: pregelatinized corn starch | 550 |
| PROTIDES: soya isolate (lacking in methionine) | 210 |
| LIPIDES: | |
| lard | 100 |
| nut oil | 10 |
| COMPLETE MINERAL SALTS | 50 |
| BALANCED VITAMIN MIXTURE | 25 |
| FIBERS: agar—agar | 55 |

The composition of Example 1 lacked 50% of the methionine. This composition was presented in the form of a powder.

In a similar manner, various compositions were prepared for mice or rats, cats, dogs or man, lacking approximately 75% of the methionine. The contents of said compositions (in g/kg of composition) are summarized in Table 2 below.

TABLE 2

| Nutritional Ingredients | Example 2 Composition for Mouse or Rat | Example 3 Composition for Cat | Example 4 Composition for Dog | Example 5 Composition for Man |
| --- | --- | --- | --- | --- |
| GLUCIDES: pregelatinized corn starch | 620 | 615 | 685 | 675 |
| PROTIDES: soya isolate | 120 | 175 | 125 | 125 |
| LIPIDES: | | | | |
| lard | 100 | 100 | 100 | 100 |
| nut oil | 10 | 10 | 10 | 10 |
| COMPLETE MINERAL SALTS | 50 | 50 | 50 | 50 |
| BALANCED VITAMIN MIXTURE | 25 | 25 | 25 | 25 |
| FIBERS: agar—agar | 75 | 25 | 5 | 10 |

The complete mineral salts used in the preceding compositions are indicated in Table 3.

TABLE 3

| | MOUSE | CAT | DOG | MAN |
| --- | --- | --- | --- | --- |
| g/kg of Composition | | | | |
| Calcium | 2.78 | 16.4 | 22 | 3.35 |
| Phosphorus | 8.25 | 11.49 | 13 | 2.75 |
| Sodium | 3.11 | 6 | 5.5 | 3.40 |
| Potassium | 6.41 | 7.4 | 6.3 | 4.05 |
| Chlorine | 2.76 | 7.3 | 2.6 | 0.46 |
| Magnesium | 1.29 | 1.89 | 2.5 | 0.87 |
| Sulfur | 1.66 | 1.24 | 1.5 | 0.98 |
| mg/kg of composition | | | | |
| Manganese | 1.2 | 121 | 56.5 | 8.4 |
| Zinc | 5.42 | 55 | 62.6 | 23 |
| Copper | 16 | 15 | 14.9 | 4.13 |
| Cobalt | 1 | 1 | 0.92 | 1 |
| Iodine | 24 | 27 | 0.75 | 0.4 |
| Iron (ferrous) | 240 | 220 | 165 | 85 |
| Fluorine | 0.6 | 0.45 | 0.5 | 0.4 |

The balanced vitamin mixtures used in the preceding compositions appear in Table 4.

TABLE 4

| mg/kg of Composition | MOUSE | CAT | DOG | MAN |
| --- | --- | --- | --- | --- |
| A | 3.48 | 17.20 | 5.36 | 5.89 |
| D | 0.125 | 0.14 | 0.05 | 0.14 |
| B1 | 15.8 | 65 | 2.3 | 5.7 |
| B2 | 20 | 45 | 5 | 7.1 |
| B6 | 15.2 | 35 | 3 | 3.89 |
| B12 | 0.02 | 0.15 | 0.02 | 0.017 |
| E | 273 | 260 | 225 | 72 |
| K3 | 5 | 10 | 3 | 4 |
| PP | 25 | 44 | 48.6 | 63.4 |
| Pantothenic Acid | 45.8 | 50 | 30 | 15 |
| Folic Acid | 2 | 4 | 0.5 | 1.04 |
| Biotin | 1 | 0.4 | 0.2 | 0.44 |
| Choline | 1500 | 3000 | 2000 | 1500 |
| C | 300 | 40 | 35 | 75 |
| INOSITOL | 850 | 300 | 300 | 236 |
| Paraaminobenzoic Acid | 100 | 100 | 100 | 100 |

EXAMPLE 6

Synthetic Composition For Enteral Use

The following composition in accordance with Table 5 (synthetic with regard to the addition of amino acids) was prepared in a similar manner. The contents are expressed in g/kg of composition.

TABLE 5

| Nutritional Ingredients | Example 6 - Composition for Mouse or Rat |
| --- | --- |
| GLUCIDES: pregelatinized corn starch | 530 |

TABLE 5-continued

| Nutritional Ingredients | Example 6 - Composition for Mouse or Rat |
|---|---|
| PROTIDES: synthesized amino acids (without methionine) | 230 |
| LIPIDES: | |
| lard | 100 |
| nut oil | 10 |
| COMPLETE MINERAL SALTS | 50 |
| BALANCED VITAMIN MIXTURE | 25 |
| FIBERS: agar—agar | 55 |

The relative contents of mineral salts and vitamins were the same as before.

The relative contents of amino acids are indicated in Table 6 below:

TABLE 6

| | | | |
|---|---|---|---|
| Arginine | 7.4 | Valine | 14.9 |
| Lysine | 15.9 | Histidine | 6.4 |
| Cysteine | 0.7 | Tyrosine | 12.4 |
| Tryptophan | 3.1 | Alanine | 6.6 |
| Glycocoll (= glycine) | 3.9 | Proline | 22.5 |
| | | Serine | 11.0 |
| Isoleucine | 11.8 | Aspartic Acid | 16.5 |
| Leucine | 20.2 | Glutamic Acid | 51.7 |
| Phenylalanine | 11.4 | Homocysteine | 4.7 |
| Threonine | 8.9 | | |

EXAMPLE 7

Synthetic composition for the parenteral treatment of humans, and its use and association with additional nutritional elements.

This is a conventional nutritional composition of amino acids and glucides for intravenous use, but the methionine is replaced by homocysteine.

The composition, in the form of an aqueous solution, has the following formula (in g/l):

| GLUCIDES | |
|---|---|
| Sorbitol | 40 |
| PROTIDES | |
| L-Arginine* | 6 |
| L-Lysine* | 8 |
| L-Tryptophan | 2.5 |
| Glycine | 6 |
| L-Isoleucine | 6.85 |
| L-Leucine | 6.25 |
| L-Phenylalanine | 9.60 |
| L-Threonine | 5 |
| L-Valine | 7.20 |
| L-Histidine* | 2 |
| L-Homocysteine | 10 |
| MINERAL SALTS | |
| g/liter of composition Sodium (in chloride form) | 0.350 |

*in hydrochloride form

This composition can be administered intravenously.

The additional nutritional elements can be administered as described below.

The mineral salts can be administered simultaneously or not, using conventional compositions for intravenous administration, for example the RONITAN (filed trademark) composition with the following formula (g/l):

| MINERAL SALTS | |
|---|---|
| Sodium | 1.495 |
| Potassium | 1.872 |
| Calcium | 0.16032 |
| Magnesium | 0.04661 |
| Chloride | 2.722 |
| Acetate | 0.590 |
| Sulfate | 0.192 |
| Lactate | 0.726 |
| Phosphate | 0.245 |

Similarly, the lipids can be administered intravenously using a conventional composition such as INTRALIPIDE (filed trademark) with the following formula (g/l):

| LIPIDES | |
|---|---|
| Purified soya oil | 100 |
| Purified egg lecithin | 12 |
| Glycerol | 22.5 |

Finally, the vitamins, including the choline, can be administered intramuscularly. For example, a commercial vitamin B12 composition can be used and a composition such as OTONEURINE (filed trademark) with the following formula can be used:

| OTONEURINE | g/l |
|---|---|
| Thiamine* or vitamin B1 | 2 |
| Riboflavin Phosphate or vitamin B2 | 0.2 |
| Pyridoxine* or vitamin B6 | 1 |
| Nicotinamide or vitamin PP | 8 |
| Histidine* | 4 |
| Tryptophan | 2 |
| Choline Citrate | 2 |

*in hydrochloride form

PHARMACOLOGICAL STUDY

The influence of the composition of Example 1 was studied on the appearance of metastases in mice $C_{57}$ Bl/6.

The formation of a primary tumor was induced in the mice by subcutaneous grafting of a fragment of tumor 3LL having a diameter of 1 mm.

In the absence of treatment, the animals died between the 21st and 25th day. Autopsies showed multiple pulmonary metastases.

Following the tumor graft, the mice with fed exclusively with the composition of Example 1, taken as desired.

The reference animals were fed with the following nonlacking composition of Table 7 below:

TABLE 7

| Ingredients | % by weight |
|---|---|
| Glucides | 53 |
| Protides | |
| Casein | 23 |
| Powdered Milk | 4 |
| Beer Yeast | 2.5 |
| Lipides | |
| Lard | 9.2 |
| Nut Oil | 0.8 |
| Mineral Salts | 5 |

TABLE 7-continued

| Ingredients | % by weight |
| --- | --- |
| Vitamins | 2.5 |

The treatments started with the grafting and lasted until the end of the experiment.

The results obtained after 21 days of treatment are summarized in Table 8 below.

The tumoral invasion was determined by counting the metastases at the surface of the lungs. The notation 100 was given to animals whose lungs were completely invaded by the metastases, rendering any counting impossible.

TABLE 8

| | Number of Pulmonary Metastases per Animal | Median Number of Pulmonary Metastases |
| --- | --- | --- |
| Full diet (reference treatment) | 100-100-100-100-100 100-100-100-38-23-28 12-8-1 | 100 |
| Diet lacking in methionine | 100-100-62-52-41* 29-25-23-22-2-1-0 | 27 |

Wilcoxon text: * $p<0.01$

It can be seen that the median number of metastases was decreased by more than 70% in relation to the references.

The treatment provoked neither deficient pathology, nor loss of weight, nor behavior problems.

Similar results were obtained on WAG rats carrying a J1 sarcoma graft (sarcoma of the pulmonary tissue). Each rat was subcutaneously injected with $10^5$ cells of the J1 clone. In this case, the nutritional treatment began when the tumor appeared, which was 15 days after the graft. In addition, the tumors were surgically removed when they reached a diameter of 14 mm.

EXAMPLE 9

METHIONINE NEEDS OF 2 CLONES OF A RHABDOMYOSARCOMA WITH A DIFFERENT METASTATIC POTENTIAL

Cells Used

F9-4/0 stock with an average metastatic potential: this F9-4/0 is a stock established from a rhabdomyosarcoma induced in the Wistar AG rat through the intramuscular injection of nickel.

This stock was then cloned and has provided different clones with a varied metastatic potential (evaluated by subcutaneous implantation in the rat).

F9-4/21 clone with a low metastatic potential
J9-4/1 very metastatic
Fr: Rat embryo fibroblasts (normal cells).

Culture Medium

Eagle medium Dulbecco modification without methionine (Eurobio).

7.5 $\mu$M of hydroxocobalamine, 0.1 mM of folic acid and 10% dialyzed calf fetal serum were added to this medium. 0.1 mM homocysteine (Met$^-$Hcy+ medium) was added to this base medium.

Protocol

The cells were seeded in 35 mm Petri dishes at a rate of $2.10^4$ cells in 2 ml of Met$^-$Hcy+medium+10% dialyzed calf fetal serum.

Various concentrations of methionine were then added:

0–0.05–0.1–0.5–0.75–1–1.5–2–2.5–3–4–5– and 30 $\mu$g/ml.

The number of cells in the culture dishes after 4 days was evaluated using a Coulter counter.

The results are expressed in % of cells present in the dishes at a concentration x methionine in relation to the number of cells present in the reference sample (30 $\mu$m/ml)

These results are shown in FIG. 1. It can be seen that the highly metastatic cells are more sensitive to the absence of methionine, even in the presence of homocysteine.

Similar results were noted with the following highly metastatic cells (human stocks):

| MCF 7 | mammary adenocarcinoma |
| --- | --- |
| HT 29 | colic adenocarcinoma |
| SCC 2 | lung cancer with small cells |
| IGR 37 | melanoma |
| A549 Asc | melanoma |
| RAJI | lymphoma |

EXAMPLE 10

PHARMACOLOGICAL STUDY IN THE RAT

A) $2.10^5$ J9-4/1 cells (highly metastatic) were injected subcutaneously. When the tumors reached a diameter of 12 mm, the animals were treated with different diets until the experiment was completed.

The female Wistar rats (2 months) were treated with diets whose composition in proteins or amino acids was the following: Casein 16%, Met$^-$HCy+16% or Met$^-$HCy- 16%, when the primary tumor reached a diameter of 12 mm and until the experiment was completed.

Evolution of the tumor

The detection of the tumor took place approximately 15 days after the graft;

The tumor reached 12 mm between the 20th and the 25th day and the metastases began to be transformed;

The linguinal axillary ganglions were detectable on the 30th day;

The animals died between the 60th and 65th day.

The autopsy showed that they had multiple pulmonary metastases.

Figure 2:
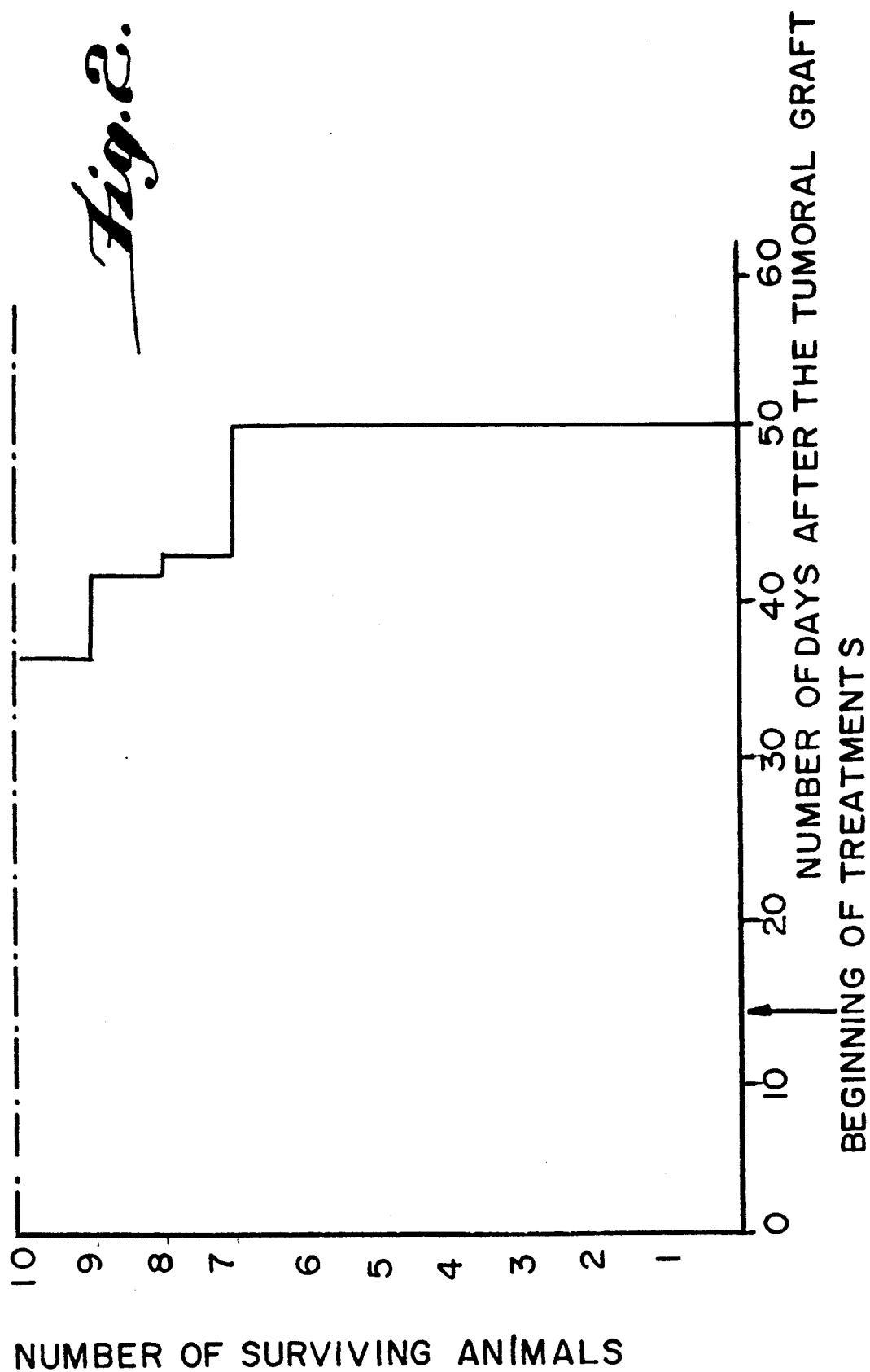

The results are summarized:
1) in Table 9:
Number of pulmonary metastases present in the animals;
2) in FIG. 2:

Graph showing the survival of animals with rhabdomyosoroma subjected to the Met$^-$HCy$^-$diet on the graph the symbol—•— represents the synthetic regimen, without methionine, with homocysteine, i.e. Met$^-$HCy+ while the symbol—represents the synthetic regimen, without methionine, without homocysteine, i.e. Met$^-$HCy$^{31}$; as compared to that of animals treated with the Met$^-$HCy+ diet;

Met$^-$HCy+: diet composed of a mixture of amino acids with a composition identical to casein. The methionine is replaced with homocysteine.

Figure 3:
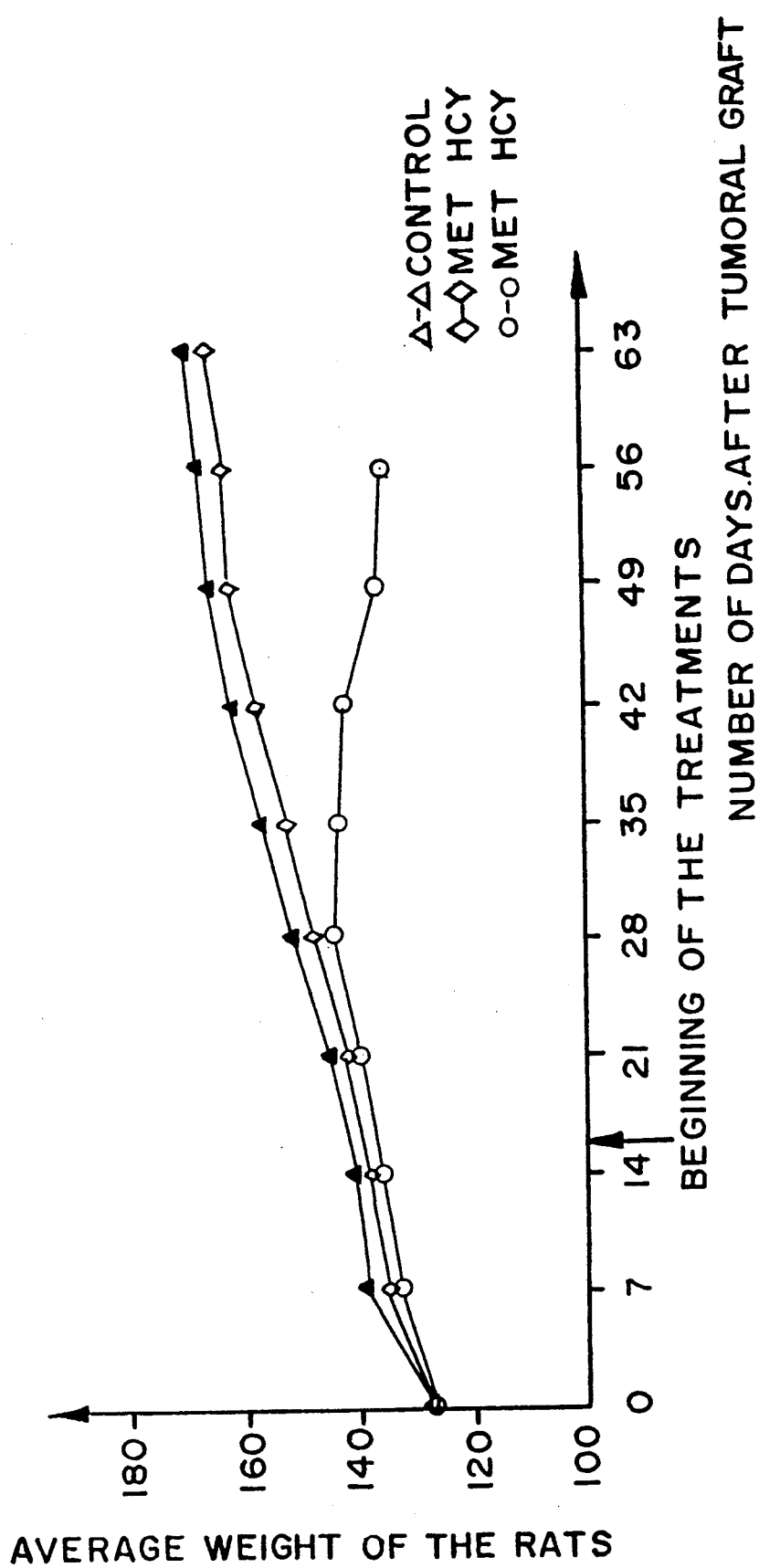

Met$^-$HCy$^-$: diet composed of a mixture of amino acids with a composition identical to casein. This diet contains neither methionine nor homocysteine, 3) in FIG. 3:
Graph showing weight curves of rats with rhabdomyosarcoma J1 subjected to regimes without methionine, with or without methionine.

CONCLUSIONS 1)
a) The diet where the methionine is substituted by homocysteine (Met⁻HCy⁺) causes a significant decrease in the number of pulmonary metastases.
b) The diet totally lacking in methionine (Met⁻HCy⁻) causes a very significant decrease in the number of metastases.

2)
a) The (Met⁻HCy⁺) diet is well tolerated by the animals. No weight loss is detectable in relation to the reference animals.
b) The (Met⁻HCy⁻) diet causes a sudden loss in the weight of the animals 10 days after the beginning of the treatment.

3) The animals subjected to the Met⁻HCy⁻ diet die more quickly than the rats subjected to the Met⁻HCy⁺ diet.

4) This experiment, which takes place at an early stage, in fact corresponds to the treatment or to the prevention of micrometastases.

TABLE 9

|  | Number of Pulmonary Metastases per Animal | Median Number of Pulmonary Metastases |
|---|---|---|
| Casein Control 16% | 2-12-14-17-20-26-27-28-28-38 40-41-44-46-50-72-88-97-111-115 | 39(2–115) |
| MET − HCY + 16% | 1-6-10-12-12-12-12-14-14-15- * 18-22-25-32-36-41-51-57-65-83 $p<0.05$ | 17(1–83) |
| MET + HCY − 16% | 0-0-0-0-3-3-4-7-12 * $p<0.01$ | 3(0–12) |

B) In another experiment, the following results were obtained:

TABLE 10

|  | Number of Pulmonary Metastases per Rat | Median Number Metastases |
|---|---|---|
| Casein 16% | 9-11-14-17-26-26 35-50-72-73 | 26 |
| MET − HCY + 16% | 1-6-6-6-9-13-13 32-32 $p<0.02$ | 9 |

In the preceding experiments, the nutritional mixture had the following composition:

TABLE 11

| BASE COMPOSITION | |
|---|---|
| Nutritional Ingredients | g/Kg of Composition |
| GLUCIDES: Pregelatinized corn starch | 685 |
| PROTIDES: Casein or Mixture of amino acids | 160 160 |
| LIPIDES: Corn oil | 10 |
| MINERAL SALTS: | 55 |
| VITAMIN MIXTURE comprising choline, folic acid and vitamin B12 | 27 |
| FIBERS: Agar—Agar | 50 |
| EXCIPIENT: | 13 |

TABLE 11-continued

| BASE COMPOSITION | |
|---|---|
| Nutritional Ingredients | g/Kg of Composition |
| Glycerol monostearate | |

C) In another experiment, using a similar diet but in which the amino acid mixtures were replaced either by casein or by soya proteins (low in methionine), the following results were obtained (Table 12):

TABLE 12

|  | Number of Pulmonary Metastases per Animal | Median Number of Pulmonary Metastases |
|---|---|---|
| Casein 10% a | 8-24-26-33-35-42 45-54-75 ns | 39 |
| Soya 12% a | 2-13-17-18-26-28ᶜ 28-33-73 $p<0.01$ | 27 |
| Soya 12% b + methionine | 27-30-32-36-38-ᶜ | 38 | a) The 10% casein diet is equivalent to the 12% soya diet from a nutritional point of view.
b) The quantity of methionine in this diet is 0.4% of the nutritional composition.
c) The difference between these two groups is statistically significant $p<0.02$ Wilcoxon test.

CONCLUSIONS:

The addition of methionine in the 12% soya diet negates the effect of said diet on the metastatic dissemination of the rhabdomyosarcoma.

The decrease of methionine in the diet of tumor-carrying rats seems to be responsible for this effect.

EXAMPLE 11

SYNTHETIC AMINO ACID COMPOSITION

| Composition for the supply of protein (man) | |
|---|---|
|  | mg/g of composition |
| Essential amino acids | |
| L Isoleucine | 40 |
| L Leucine | 70 |
| L Lysine | 55 |
| L Cysteine | 5 |
| L Phenylalanine | 40 |
| L Tyrosine | 30 |
| DL Threonine | 40 |
| L Tryptophan | 10 |
| L Valine | 50 |
| DL Homocysteine | 20 |
| Non-essential amino acids | |
| L Arginine | 80 |
| L Histidine | 30 |
| L Alanine | 60 |
| L Aspartic acid | 110 |
| L Glutamic acid | 190 |
| Glycine | 20 |
| L Proline | 100 |
| L Serine | 50 |

This composition, which can be diluted in water, is administered in an amount of 1 g/kg of weight/day, as a protein supply.

We claim:
1. A synthetic or semi-synthetic nutritional composition, for inhibiting the development and dissemination of malignant tumors in a human,
    said composition containing, as the source of amino acids, a mixture of essential amino acids in appro- priate proportions so as to constitute a balanced nutritional composition for the said mammal, but containing a methionine content reduced by x %, with x being at least 50, said composition additionally containing homocysteine, it being understood that said reduced methionine content is a content of $$\frac{y(100-x)}{100} \%$$

by weight, wherein y is the % by weight methionine content which is normally present in a balanced nutritional composition for the said human.

2. The composition of claim 1, wherein the other ingredients of the composition are free of proteins, or do not contain more than 1% thereof, based on the total dry weight of the constituents.

3. The composition of claim 1, wherein the methionine content of said mixture is 0%.

4. The composition of claim 1, wherein the molar amount of homocysteine is equal to the molar amount of the lacking methionine, said molar amount being equal to the molar amount corresponding to $$\frac{xy}{100} \%$$

by weight of methionine.

5. The composition of claim 1, wherein the homocysteine is contained in microcapsules having walls which are soluble in the digestive tract, and wherein said composition is for enteral administration.

6. A semi-synthetic nutritional composition, for inhibiting the development and dissemination of malignant tumors in a human, said composition containing, as the partial or sole source of amino acids, proteins having a low methionine content, so that the composition contains essential amino acids in appropriate proportions so as to constitute a balanced nutritional composition for the said mammal, but with a methionine content reduced by x %, with x being at least 50, said composition additionally containing homocysteine, it being understood that said reduced methionine content is a content of $$\frac{y(100-x)}{100} \%$$

by weight, wherein y is the % by weight methionine content which is normally present in balanced nutritional composition for the said human.

7. A method of therapeutic treatment for inhibiting the development and dissemination of malignant tumors in human, comprising of administering to a patient, enterally or parenterally, a composition as defined in claim 1 in an amount sufficient to satisfy nutritional needs.

8. A method of therapeutic treatment for inhibiting the development and dissemination of malignant tumors in human, comprising of administering to a patient, enterally or parenterally, a composition as defined in claim 1 in an amount sufficient to satisfy nutritional needs and also administering choline to said patient.

9. A method of therapeutic treatment for inhibiting the development and dissemination of malignant tumors in human comprising of administering to a patient, enterally or parenterally, a composition as defined in claim 3 in an amount sufficient to satisfy nutritional needs.

10. A method of therapeutic treatment for inhibiting the development and dissemination of malignant tumors in human comprising of administering to a patient, enterally or parenterally, a composition as defined in claim 4 in an amount sufficient to satisfy nutritional needs.

11. A method of therapeutic treatment for inhibiting the development and dissemination of malignant tumors in human, comprising of administering to a patient enterally a composition as defined in claim 6 in an amount sufficient to satisfy nutritional needs.

12. A method of therapeutic treatment for inhibiting the development and dissemination of metastases, or for preventing the implantation of metastases and/or for treating micrometastases in humans, comprising of administering to a patient, enterally or parenterally, a composition as defined in claim 1, in an amount sufficient to satisfy nutritional needs.

13. A method of therapeutic treatment for inhibiting the development and dissemination of metatases, or for preventing the implantation of metastases and/or for treating micrometastases in human comprising of administering to a patient, enterally or parenterally, a composition as defined in claim 1 in an amount sufficient to satisfy nutritional needs and also administering choline to said patient.

14. A method of therapeutic treatment for inhibiting the development and dissemination of metastases, or for preventing the implantation of metastases and/or for treating micrometastases in humans, comprising of administering to a patient, enterally or parenterally, a composition as defined in claim 3 in an amount sufficient to satisfy nutritional needs.

15. A method of therapeutic treatment for inhibiting the development and dissemination of metastases, or for preventing the implantation of metastases and/or for treating micrometastases in humans comprising of administering to a patient, enterally or parenterally, a composition as defined in claim 4

16. A method of therapeutic treatment for inhibiting the development and dissemination of metastases, or for preventing the implantation of metastases and/or for treating micrometastases in humans comprising of administering to a patient, enterally or parenterally, a composition as defined in claim 6 in an amount sufficient to satisfy nutritional needs.

17. A process for improving the organoleptic properties of an enterally administrable synthetic or semisynthetic nutritional composition for a human, said composition containing, as the source of amino acids, a mixture of essential amino acids in appropriate proportions so as to constitute a balanced nutritional composition for said human, but containing a methionine content reduced by x%, with x being at least 50, it being understood that said reduced methionine content is a content of $$\frac{y(100-x)}{100} \%$$

% by weight, wherein y is the % by weight methionine content which is normally present in a balanced nutritional composition for the said human, said process comprising adding to said composition, at the time of administration to said human, a homocysteine composition consisting essentially of homocysteine coated by microcapsules having walls which are soluble in the digestive tract of said human.

18. A homocysteine composition consisting essentially of homocysteine coated by microcapsules having walls which are soluble in the digestive tract of a human.

19. A synthetic or semi-synthetic nutritional composition for a human, said composition containing
   (a) as the source of amino acids, a mixture of essential amino acids in appropriate proportions so as to constitute a balanced nutritional composition for said human, but containing a methionine content reduced by x%, with x being at least 50, it being understood that said reduced methionine content is a content of $$\frac{y(100-x)}{100} \%$$

by weight, wherein y is the % by weight of methionine content which is normally present in a balanced nutritional composition for the said human
   (b) homocysteine in a molar amount equal to the molar amount of the lacking methionine, said molar amount being equal to the molar amount corresponding to $$\frac{xy}{100} \%$$

by weight of methionine, and
   (c) choline.

20. A process for inhibiting the development and dissemination of malignant tumors in a human comprising
   (a) administering to said human a synthetic or semi-synthetic nutritional composition, said composition containing
      (a') as the source of amino acids a mixture of essential amino acids in appropriate proportions so as to constitute a balanced nutritional composition for said human, but containing a methionine content reduced by x%, with x being at least 50, it being understood that said reduced methionine content is a content of $$\frac{y(100-x)}{100} \%$$

by weight, wherein y is the % by weight methionine content which is normally present in a balanced nutritional composition for the said human, and
      (b') homocysteine in a molar amount equal to the molar amount of the lacking methionine, said molar amount being equal to the molar amount corresponding to $$\frac{xy}{100} \%$$

by weight of methionine, and
   (b) separately administering choline to said human.

21. The composition of claim 6 wherein the molar amount of homocysteine is equal to the molar amount of the lacking methionine, said molar amount being equal to the molar amount corresponding to $$\frac{xy}{100} \%$$

by weight of methionine.

22. The method of claim 9 which also includes administering choline to said patient.

23. The method of claim 10 which also includes administering choline to said patient.

24. The method of claim 11 which also includes administering choline to said patient.

25. The method of claim 12 which also includes administering choline to said patient.

26. The method of claim 14 which also includes administering choline to said patient.

27. The method of claim 15 which also includes administering choline to said patient.

28. The method of claim 16, which also includes administering choline to said patient.

* * * * *